(12) United States Patent
Kahook

(10) Patent No.: US 10,828,196 B2
(45) Date of Patent: Nov. 10, 2020

(54) OCULAR TREATMENT DEVICES AND RELATED METHODS OF USE

(71) Applicant: NEW WORLD MEDICAL, INC., Rancho Cucamonga, CA (US)

(72) Inventor: Malik Y. Kahook, Denver, CO (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 0 days.

(21) Appl. No.: 16/727,767

(22) Filed: Dec. 26, 2019

(65) Prior Publication Data

US 2020/0129335 A1    Apr. 30, 2020

Related U.S. Application Data

(63) Continuation of application No. 15/847,770, filed on Dec. 19, 2017, now Pat. No. 10,543,122.
(Continued)

(51) Int. Cl.
*A61F 9/007* (2006.01)
*A61F 9/00* (2006.01)

(52) U.S. Cl.
CPC ........ *A61F 9/00781* (2013.01); *A61F 9/0017* (2013.01)

(58) Field of Classification Search
CPC .......... A61M 5/46; A61M 5/48; A61M 5/488; A61M 5/329; A61M 5/3297; A61M 5/3286; A61M 2005/3201; A61F 9/00745; A61F 9/007; A61F 9/017; A61F 9/00736; A61F 9/00763; A61F 9/00781; A61F 9/00709; A61F 9/00; A61F 9/0017; A61F 9/00754; A61F 9/00718; A61F 9/0008; A61B 17/320725; A61B 17/320758; A61B 17/221; A61B 17/32053;
(Continued)

(56) References Cited

U.S. PATENT DOCUMENTS

| | | |
|---|---|---|
| 3,439,675 A | 4/1969 | Cohen |
| 4,373,526 A | 2/1983 | Kling |

(Continued)

FOREIGN PATENT DOCUMENTS

| | | |
|---|---|---|
| CN | 105919724 | 9/2016 |
| DE | 29909787 | 9/1999 |

(Continued)

OTHER PUBLICATIONS

International Search Report and Written Opinion for Application No. PCT/US17/67126, dated Apr. 24, 2018, 14 pages.
(Continued)

*Primary Examiner* — Tiffany Legette
(74) *Attorney, Agent, or Firm* — Morgan, Lewis & Bockius LLP

(57) ABSTRACT

Apparatus and methods for ocular treatment are provided. The apparatus can comprise a microcannula having a proximal end, a distal end, a cavity, and a central longitudinal axis. The apparatus can include a handle coupled to the proximal end of the microcannula. The apparatus can include multiple orifices extending circumferentially about the microcannula distal end, each of the orifices defining a channel extending transverse to the central longitudinal axis, and one or more grooves about a circumference of the microcannula.

18 Claims, 11 Drawing Sheets

Related U.S. Application Data

(60) Provisional application No. 62/436,099, filed on Dec. 19, 2016.

(58) Field of Classification Search
CPC ....... A61B 2017/320072; A61B 2017/320088; A61B 2017/32007
See application file for complete search history.

(56) References Cited

U.S. PATENT DOCUMENTS

| | | | |
|---|---|---|---|
| 4,401,124 A | 8/1983 | Guess et al. | |
| 4,699,612 A | 10/1987 | Hamacher | |
| 4,764,165 A | 8/1988 | Reimels et al. | |
| 4,795,446 A | 1/1989 | Fecht | |
| 4,904,238 A | 2/1990 | Williams | |
| 4,940,468 A | 7/1990 | Petillo | |
| 4,955,883 A * | 9/1990 | Nevyas | A61B 18/082 606/28 |
| 5,407,441 A | 4/1995 | Greenbaum | |
| 5,449,351 A | 9/1995 | Zohmann | |
| 5,487,725 A | 1/1996 | Peyman | |
| 5,681,291 A | 10/1997 | Galli | |
| 5,755,700 A | 5/1998 | Kritzinger et al. | |
| 5,848,996 A | 12/1998 | Eldor | |
| 6,102,896 A | 8/2000 | Roser | |
| 6,126,629 A | 10/2000 | Perkins | |
| 6,135,984 A | 10/2000 | Dishler | |
| 6,162,202 A | 12/2000 | Sicurelli et al. | |
| 6,375,648 B1 | 4/2002 | Edelman et al. | |
| 6,413,245 B1 | 7/2002 | Yaacobi et al. | |
| 6,494,868 B2 | 12/2002 | Amar | |
| 6,613,026 B1 | 9/2003 | Palasis et al. | |
| 6,802,829 B2 | 10/2004 | Buono | |
| 6,969,373 B2 | 11/2005 | Schwartz et al. | |
| 7,141,048 B1 | 11/2006 | Charles | |
| 7,361,158 B1 | 4/2008 | Mooney, Jr. | |
| 7,931,622 B2 | 4/2011 | Beling et al. | |
| 7,998,108 B2 | 8/2011 | Nazzaro et al. | |
| 8,529,541 B2 | 9/2013 | Klein | |
| 8,608,632 B1 | 12/2013 | Brigatti et al. | |
| 8,622,977 B2 | 1/2014 | Persat | |
| 9,050,167 B2 | 6/2015 | Akahoshi | |
| 9,220,850 B2 | 12/2015 | Kawamoto et al. | |
| 9,233,195 B2 | 1/2016 | Akahoshi | |
| 9,439,807 B2 | 9/2016 | Koplin | |
| 9,440,050 B2 | 9/2016 | Katase et al. | |
| 9,457,183 B2 | 10/2016 | Sallberg et al. | |
| 9,486,583 B2 | 11/2016 | Lannan et al. | |
| 9,498,377 B2 | 11/2016 | McCary et al. | |
| 9,592,352 B2 | 3/2017 | Matsuzawa | |
| 2002/0111608 A1* | 8/2002 | Baerveldt | A61F 9/00781 606/6 |
| 2004/0147883 A1 | 7/2004 | Tsai | |
| 2005/0020990 A1 | 1/2005 | Akahoshi | |
| 2005/0197633 A1* | 9/2005 | Schwartz | A61M 5/158 604/264 |
| 2006/0047254 A1 | 3/2006 | Akahoshi | |
| 2006/0100653 A1* | 5/2006 | Akahoshi | A61F 9/00745 606/169 |
| 2006/0223026 A1 | 10/2006 | Kuroiwa et al. | |
| 2006/0259006 A1 | 11/2006 | McKay et al. | |
| 2006/0259008 A1 | 11/2006 | Orilla | |
| 2006/0276552 A1 | 12/2006 | Barbut | |
| 2007/0078435 A1* | 4/2007 | Stone | A61M 25/0084 604/507 |
| 2007/0118142 A1 | 5/2007 | Krueger et al. | |
| 2007/0282254 A1 | 12/2007 | Chow | |
| 2008/0082078 A1 | 4/2008 | Berlin | |
| 2008/0172012 A1 | 7/2008 | Hiniduma-Lokuge et al. | |
| 2008/0249522 A1 | 10/2008 | Pappone et al. | |
| 2009/0099478 A1 | 4/2009 | Cassells et al. | |
| 2010/0100029 A1 | 4/2010 | Maskin | |
| 2010/0121284 A1 | 5/2010 | Hexsel | |
| 2010/0324530 A1 | 12/2010 | Hertzog | |
| 2011/0034864 A1* | 2/2011 | Dacquay | A61M 3/0212 604/28 |
| 2011/0046600 A1 | 2/2011 | Crank | |
| 2011/0092885 A1 | 4/2011 | Myoshi | |
| 2012/0095404 A1 | 4/2012 | Massengale et al. | |
| 2012/0253297 A1* | 10/2012 | Matsuzawa | A61M 5/158 604/272 |
| 2013/0253438 A1 | 9/2013 | Badawi et al. | |
| 2014/0081194 A1 | 3/2014 | Burns et al. | |
| 2014/0100426 A1 | 4/2014 | Barbour | |
| 2015/0051581 A1 | 2/2015 | Andino et al. | |
| 2015/0209180 A1* | 7/2015 | Prausnitz | A61F 9/0017 604/521 |
| 2015/0223977 A1 | 8/2015 | Oberkircher et al. | |
| 2015/0335487 A1 | 11/2015 | de Juan, Jr. | |
| 2015/0342784 A1 | 12/2015 | Seiler et al. | |
| 2016/0045707 A1 | 2/2016 | Conti | |
| 2016/0106461 A1 | 4/2016 | Morris | |
| 2016/0303333 A1 | 10/2016 | Momose | |
| 2017/0007776 A1 | 1/2017 | Sahin | |

FOREIGN PATENT DOCUMENTS

| | | | |
|---|---|---|---|
| DE | 102005049791 | 4/2007 | |
| DE | 102009049153 | 4/2011 | |
| DE | 202011100654 | 10/2011 | |
| FR | 2986419 | 8/2013 | |
| FR | 3012041 | 4/2015 | |
| GB | 858913 | 1/1961 | |
| GB | 2202747 | 10/1988 | |
| WO | WO-1990001349 | 2/1990 | |
| WO | WO-9218174 A1 * | 10/1992 | .......... A61M 25/065 |
| WO | WO-1997014454 | 4/1997 | |
| WO | WO-2002058607 | 8/2002 | |
| WO | WO-2010026644 | 3/2010 | |
| WO | WO-2011057830 | 5/2011 | |
| WO | WO-2011141940 | 11/2011 | |
| WO | WO-2013158919 | 10/2013 | |
| WO | WO-2014061030 | 4/2014 | |
| WO | WO-2016133334 | 8/2016 | |
| WO | WO-2016192739 | 12/2016 | |
| WO | WO-2017053572 | 3/2017 | |
| WO | WO-2017168015 | 10/2017 | |

OTHER PUBLICATIONS

Tran Canula.RTM. Technical Sheet, fabrinal Eye Care, 2018, retrieved from http://fabrinal.ch/pdf/63/technical-sheet-tran_canula_e_b08.2018.pdf.

Extended European Search Report for Application No. 17884992.3, dated Jul. 16, 2020, 9 pages.

* cited by examiner

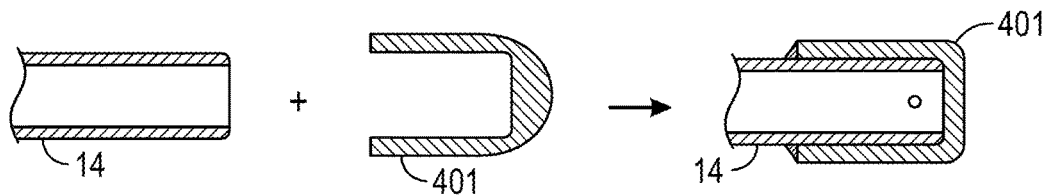
FIG. 4B  FIG. 4C
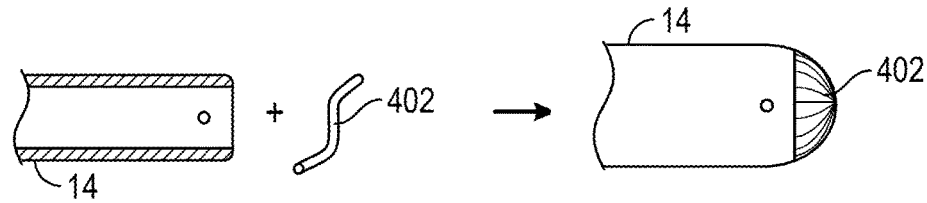
FIG. 4D  FIG. 4E
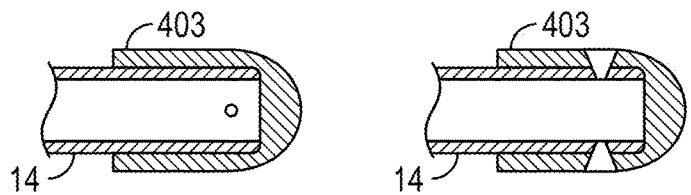
FIG. 4F  FIG. 4G
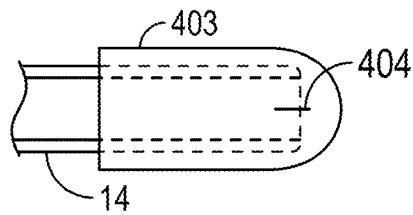
FIG. 4H
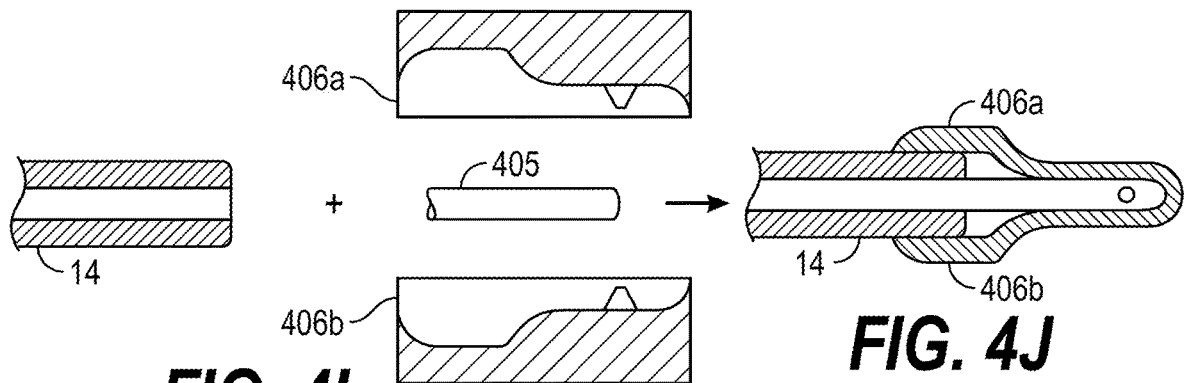
FIG. 4I  FIG. 4J

OCULAR TREATMENT DEVICES AND
RELATED METHODS OF USE

RELATED APPLICATIONS

This application is a continuation of U.S. patent application Ser. No. 15/847,770, titled "OCULAR TREATMENT DEVICES AND RELATED METHODS OF USE," and filed on Dec. 19, 2017, now U.S. Pat. No. 10,543,122, issued on Jan. 28, 2020, which claims the benefit of priority under 35 U.S.C. § 119(e) of U.S. Provisional Application No. 62/436,099, titled "OCULAR TREATMENT DEVICES AND RELATED METHODS OF USE," and filed on Dec. 19, 2016, the entirety of which are incorporated herein by reference.

TECHNICAL FIELD

Various aspects of the present disclosure relate generally to ocular tissue treatment. More specifically, the present disclosure relates to instruments and related methods for reducing intraocular eye pressure.

INTRODUCTION

Glaucoma is a disease resulting from an increase in intraocular eye pressure (TOP). IOP may increase when natural drainage of the eye (e.g., drainage of the humus of the eye) is prevented, reduced, or otherwise blocked. Cavities in front of (e.g., on top of) the lens of the eye are filled with a viscous fluid called aqueous humor. A continuous flow of aqueous humor through the eye provides nutrition to portions of the eye (e.g., the cornea and the lens) that have no blood vessels. This flow of aqueous humor also removes waste (e.g., foreign object debris) from these tissues. In a healthy eye, a stream of aqueous humor drains out of the anterior chamber of the eye through the trabecular meshwork and into Schlemm's canal as new aqueous humor is secreted by the epithelial cells of the ciliary body. The drained aqueous humor enters the venous blood stream from Schlemm's canal and is carried along with the venous blood leaving the eye. When the natural drainage mechanisms of the eye (e.g., Schlemm's canal and/or the trabecular meshwork) stop functioning properly, the IOP begins to increase.

Prior treatments to reduce IOP may include application of eye drops and other medications. Application of such medications may be required multiple times a day, and may interfere with a patient's quality of life. Additionally, laser treatments and other surgical applications may be used to reduce TOP, however, such treatments may be invasive and often provide only temporary reduction of TOP.

The systems, devices, and methods of the current disclosure may rectify some of the deficiencies described above or address other aspects of the prior art.

SUMMARY

At least one aspect is directed to a medical device. The medical device includes a microcannula having a proximal end, a distal tip, and a cavity, the microcannula having a central longitudinal axis. The medical device includes a handle coupled to the proximal end of the microcannula. The microcannula includes multiple orifices extending circumferentially about the distal tip, each orifice defining a channel extending transverse to the central longitudinal axis and having a radially outer end positioned radially farther away from the central longitudinal axis than a radially inner end, and each orifice configured to deliver a substance radially outwardly from the distal tip of the microcannula. The medical device also includes a plurality of grooves about a circumference of the microcannula, wherein an inner diameter of the microcannula tapers down from a first position of the microcannula to a second position of the microcannula closer to the distal tip than the first position.

In some implementations, an outer diameter of the microcannula varies along a length of the microcannula.

In some implementations, the inner diameter of the microcannula varies along a length of the microcannula at a same rate as an outer diameter of the microcannula varies along the length of the microcannula.

In some implementations, a first orifice among the multiple orifices is spaced 180 degrees apart from a second orifice among the multiple orifices.

In some implementations, each of the plurality of grooves has a depth between 15 μm and 35 μm.

In some implementations, each of the plurality of grooves is formed proximal to the orifices.

In some implementations, the substance is a viscoelastic fluid, wherein the handle comprises a reservoir containing the viscoelastic fluid, and an actuator configured to eject the viscoelastic fluid radially outwardly through the orifices.

In some implementations, the radially outer end is positioned distal to the radially inner end, such that each of the orifices is configured to deliver the substance distally and radially outwardly from the microcannula.

At least one aspect is directed to a medical device that includes a first cannula having a distal end, and a cavity, the first cannula having a central longitudinal axis, and one or more protrusions, the one or more protrusions of the first cannula extend circumferentially at the distal end of the first cannula and are located in the cavity of the first cannula. The medical device includes a second cannula having a proximal end, a distal tip, and a cavity, the second cannula being a microcannula moveably housed within the first cannula and has a central longitudinal axis, and one or more protrusions located on an outer circumferential surface of the second cannula. The multiple orifices extending circumferentially about the distal tip of the microcannula, each orifice defining a channel extending transverse to the central longitudinal axis and having a radially outer end positioned radially farther away from the central longitudinal axis than a radially inner end, and each orifice configured to deliver a substance radially outwardly from the distal tip of the microcannula. The medical device also includes a plurality of grooves about a circumference of the second cannula, wherein an inner diameter of the second cannula tapers down from a first position of the second cannula to a second position of the second cannula closer to the distal tip than the first position.

In some implementations, a first orifice among the multiple orifices is positioned parallel to a second orifice among the multiple orifices.

In some implementations, the plurality of grooves are located at the distal tip of the second cannula.

In some implementations, the plurality of grooves are equidistantly spaced apart.

In some implementations, the one or more protrusions of one of the first cannula and the second cannula include multiple protrusions equidistantly spaced apart.

In some implementations, the one or more protrusions of the second cannula are proximal to the one or more protrusions of the first cannula when the distal tip of the second cannula is within the first cannula.

In some implementations, the one or more protrusions of the second cannula are distal to the one or more protrusions of the first cannula when at least a portion of the distal tip of the second cannula is moved outside of the distal end of the first cannula.

At least one aspect is directed to a method of delivering fluid. The method includes inserting a microcannula through an incision in an anterior chamber of an eye, the microcannula including a proximal end, a distal tip, and a cavity, the microcannula having a central longitudinal axis with the proximal end of the microcannula being coupled to a handle, wherein an inner diameter of the microcannula tapers down from a first position of the microcannula to a second position of the microcannula closer to the distal tip than the first position. The method also includes advancing the microcannula distal tip through a trabecular meshwork of the eye and into Schlemm's canal of the eye. The method further includes delivering fluid through multiple orifices each of which being positioned within the Schlemm's canal, the multiple orifices extending circumferentially about the distal tip of the microcannula, each orifice defining a channel extending transverse to the central longitudinal axis and having a radially outer end positioned radially farther away from the central longitudinal axis than a radially inner end such that the fluid is delivered radially outwardly from the distal tip of the microcannula.

In some implementations, a plurality of grooves are located at the distal tip of the microcannula.

In some implementations, the microcannula includes one or more protrusions located on an outer circumferential surface of the microcannula. The microcannula is movably housed within a second cannula, the second cannula having one or more protrusions extending circumferentially at a distal end of the second cannula and located in a cavity of the second cannula.

In some implementations, the step of advancing the distal tip of the microcannula further comprises applying a force to the microcannula to move the one or more protrusions of the microcannula distal to the one or more protrusions of the second cannula.

In some implementations, delivering the fluid through the multiple orifices includes delivering the fluid into the Schlemm's canal and one or more layers of the trabecular meshwork.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 4B-4J illustrate cross-sectional view of a tip of microcannula of the device of FIG. 1, according to an illustrative implementation.

DETAILED DESCRIPTION

The following detailed description is exemplary and explanatory only and is not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value. The term "distal" refers to a portion farthest away from a user when introducing a device into a subject. By contrast, the term "proximal" refers to a portion closest to the user when placing the device into the subject.

Figure 1:
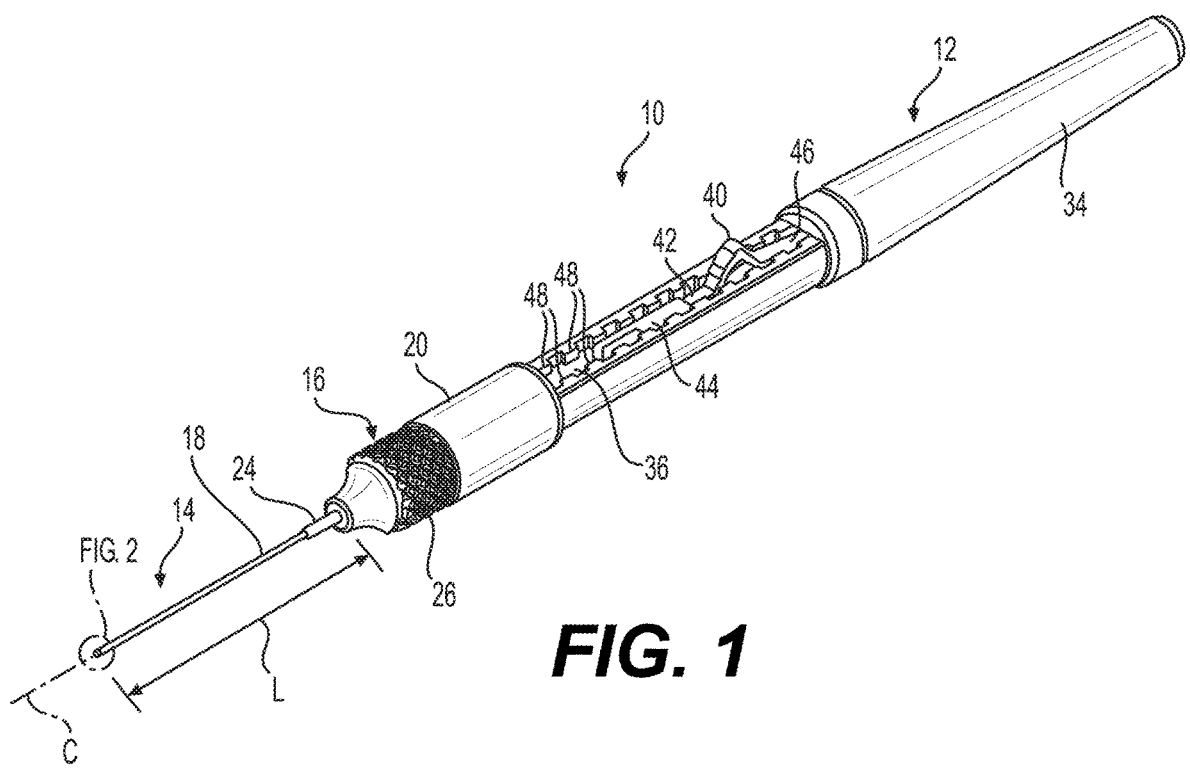
FIG. 1 illustrates an exemplary device having a handle and a microcannula, according to aspects of the disclosure.

As shown in FIG. 1, an exemplary device 10 includes a handle 12 coupled to a microcannula 14 via a connector 16. For example, a proximal end 18 or region of microcannula 14 is coupled to a distal end 20 or region of handle 12 via connector 16. Connector 16 includes a lumen 22 (FIG. 3A) extending through a reinforcement shaft or tube 24 and a connector body 26. A proximal end of connector 16 may be threadably or otherwise fixedly coupled to distal end 20 of handle 12, while proximal end 18 of microcannula 14 extends through lumen 22 of connector 16 and is fixedly coupled (e.g., glued, welded, or otherwise secured) to connector 16. In such a manner, microcannula 14 is fixedly coupled to handle 12.

A radially outer circumferential surface of connector body 26 may be knurled, ribbed, or otherwise textured to enhance a medical professional's grasp of handle 12. In some arrangements, at least one of connector 16 and distal end 20 includes a fluid luer port (not shown). The fluid luer port may extend radially away from connector 16 and/or distal end 20, and may be configured for connection to interchangeable external reservoirs. In such a manner, a reservoir 28 (FIG. 3A) positioned within handle 12, may be selectively refilled as needed or desired by a medical professional, as will be described in further detail below.

Figure 2A:
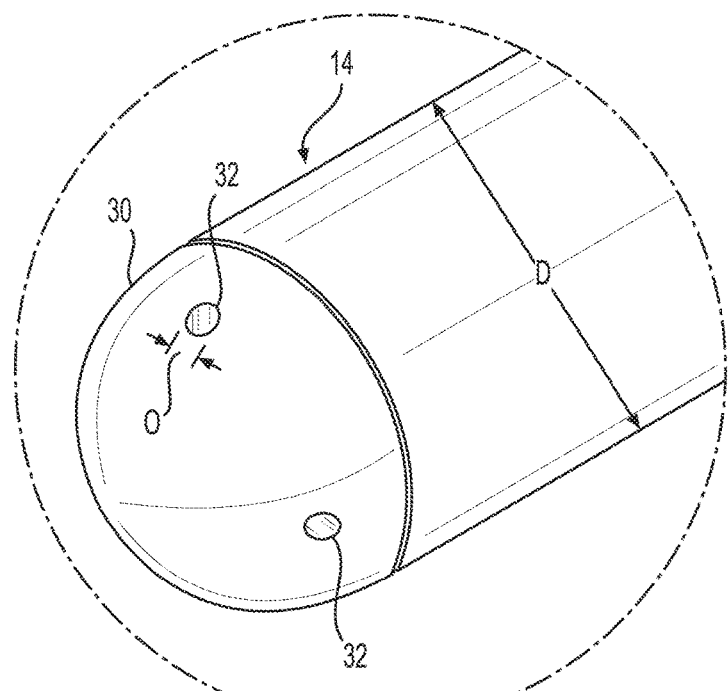
FIG. 2A is an enlarged view of a microcannula of the device of FIG. 1, according to an illustrative implementation.
Figure 2B:
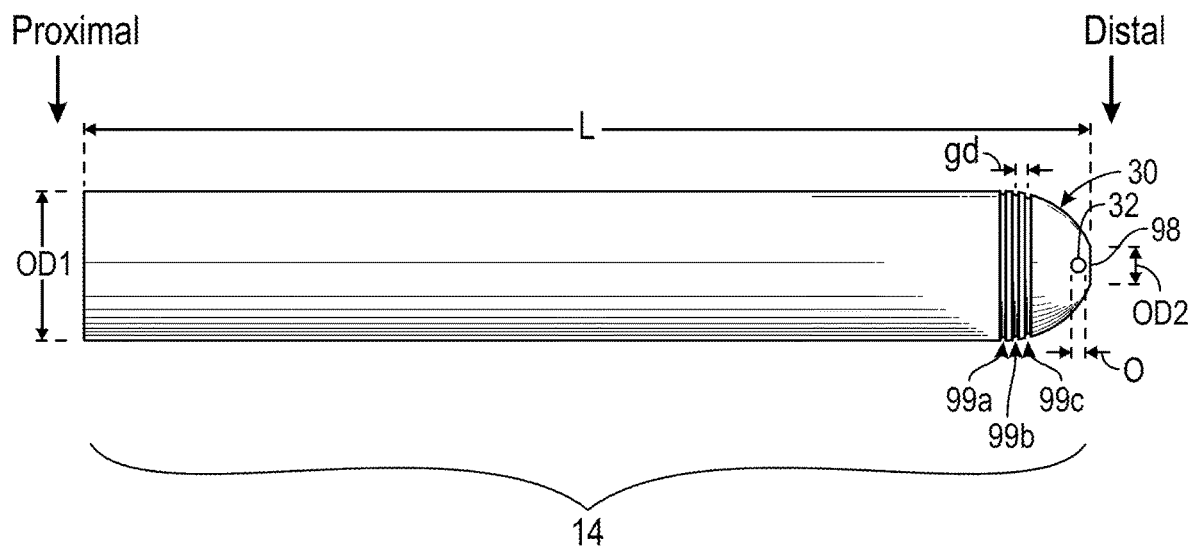
FIG. 2B is an enlarged view of a microcannula of the device of FIG. 1, according to an illustrative implementation.

As shown in FIG. 1, microcannula 14 includes a working length L, e.g., a length extending between a proximal end of tube 24 and a distal-most end of microcannula 14 between about 30 mm and about 40 mm. In some implementations, working length L may be about 36.150 mm. In some implementations, the working length L may be about 20 mm. As shown in FIG. 2A, in some implementations, a diameter D of microcannula 14 may be between about 500 μm and about 600 μm. A distal end 30 of microcannula 14 is rounded or otherwise atraumatic (e.g., blunt, unsharpened, etc.) and includes a plurality of orifices 32. For example, distal end 30 of microcannula 14 includes four orifices 32 (only two orifices 32 being visible in FIG. 2A) equidistantly spaced about a circumference of distal end 30. Each orifice 32 may have an orifice diameter O, between 30 μm and 70 μm. In some implementations, diameter O of each orifice 32 is about 50 μm. In some implementations, diameter O of each orifice 32 is about 60 μm While four equidistantly spaced orifices 32 are illustrated and described, in other arrangements, more or less orifices 32 may be positioned about the circumference of distal end 30 and may be equidistantly or non-equidistantly spaced. For example, as shown in FIG. 2B, the distal end 30 includes two orifices 32. In some implementations, orifices 32 are positioned about 180 degrees apart from each other about the circumference of distal end 30, as shown in FIG. 2B (only one of the two orifices 32 being visible in FIG. 2B). Additionally, in some arrangements, orifices 32 may be positioned at varying axial locations along distal end 30. In some implementations, orifices 32 are arranged for delivery of a fluid (e.g., liquid or gas) or other substance from a reservoir 28 (FIG. 3A) and extend at an angle non-perpendicular to a central axis C of microcannula 14, as will be described in further detail below. In some implementations, orifices 32 are arranged for delivery of a fluid or other substance from the reservoir 28 and extend at an angle perpendicular to the central axis C of microcannula 14.

In some implementations, microcannula 14 may have an outer diameter with varying sizes along the length of the microcannula 14. For example, as shown in FIG. 2B, outer diameter OD1 near the proximal end of microcannula 14 may be between about 500 μm and about 700 μm, such as about 600 μm, and outer diameter OD2 near the distal end of microcannula 14 may be between about 100 μm and about 200 μm, such as about 150 μm. The outer diameter of microcannula 14 may taper down near a terminal end of microcannula 14. For example, in FIG. 2B, the outer diameter OD1 of microcannula 14 is tapered down to OD2 near the terminal end 98 of microcannula 14. A first outer diameter of microcannula 14 may taper down starting from a certain distance away from a terminal end of microcannula 14. For example, in FIG. 2B, the outer diameter OD1 may be tapered down starting from 350 μm away from the terminal end 98 of microcannula 14. A first outer diameter of microcannula 14 may be gradually tapered down to a second outer diameter. For example, in FIG. 2B, starting from 350 μm away from the terminal end 98 of microcannula 14, the outer diameter OD1 is tapered down gradually from 600 μm to the outer diameter OD2 of 150 μm near the terminal end 98.

Microcannula 14 may have an inner diameter with varying sizes along the length of the microcannula 14. For example, an inner diameter near the proximal end of microcannula 14 may be between about 300 μm and 500 μm, such as 400 μm, and an inner diameter near the distal end of the microcannula 14 may be of a different size than the inner diameter near the proximal end. In some implementations, the inner diameter of microcannula 14 may be tapered down from the inner diameter near the proximal end to the inner diameter near the distal end starting from a certain distance away from the terminal end of microcannula 14. In some implementations, the inner diameter of microcannula 14 may be tapered down starting from the location of a circumferential groove on the microcannula 14, for example, a circumferential groove closest to the proximal end of microcannula 14, such as circumferential groove 99a in FIG. 2B. In some implementations, the inner diameter of microcannula 14 is tapered down at the same rate as the outer diameter of microcannula 14 is tapered down, such that the ratio between the size of the outer diameter and the size of the inner diameter is constant or near constant. In some implementations, inner diameter of microcannula 14 is tapered down starting from the same location on the microcannula 14 as outer diameter of microcannula 14 is tapered down. For example, as described above, outer diameter of microcannula 14 may be tapered down from OD1 starting from a location on microcannula 14 that is 350 μm away from terminal end 98 of microcannula 14, and similarly, inner diameter of microcannula 14 may be tapered down from a first size starting from a location that is 350 μm away from the terminal end 98 of microcannula 14.

Figure 2C:
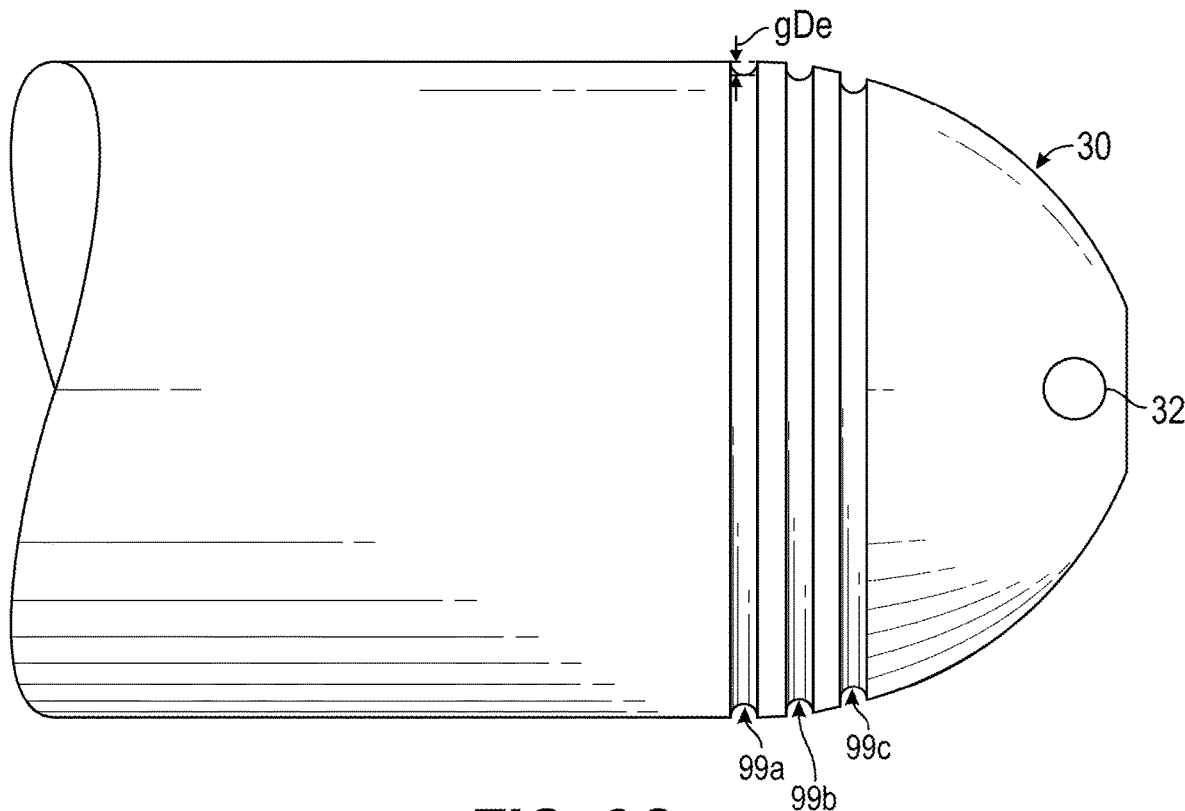
FIG. 2C is an enlarged view of the tip of the microcannula of FIG. 2B, according to an illustrative implementation.

Microcannula 14 may include one or more grooves about the circumference of microcannula 14 (referred to herein as "circumferential grooves"), such as circumferential grooves 99a, 99b, 99c. In some implementations, as shown in FIG. 2B and FIG. 2C, microcannula 14 include three such circumferential grooves. Each circumferential groove may be spaced apart from another circumferential groove on microcannula 14 by a distance gd, as shown in FIG. 2B. The distance gd may be between about 40 μm and about 60 μm. For example, the distance gd between circumferential grooves 99a, 99b, and 99c in FIG. 2B may be about 50 μm. Each circumferential groove may be of depth gDe, as shown in FIG. 2C. The depth gDe may be between about 15 μm and 35 μm. In some implementations, circumferential grooves have depth gDe of 25 μm. As shown in FIG. 2B, circumferential grooves may be formed near the distal end of microcannula 14. In some implementations, circumferential grooves may be formed starting from a location on microcannula 14 that is between about 500 μm away and 250 μm away from the terminal end 98 of microcannula 14, for example, starting from about 350 μm away from the terminal end 98 of microcannula 14. In some implementations, the distal portion of the microcannula 14, starting from a location on microcannula 14 that is between about 500 μm away and 250 μm away from terminal end 98 of microcannula 14, is configured to be a rough shaft.

Figure 2D:
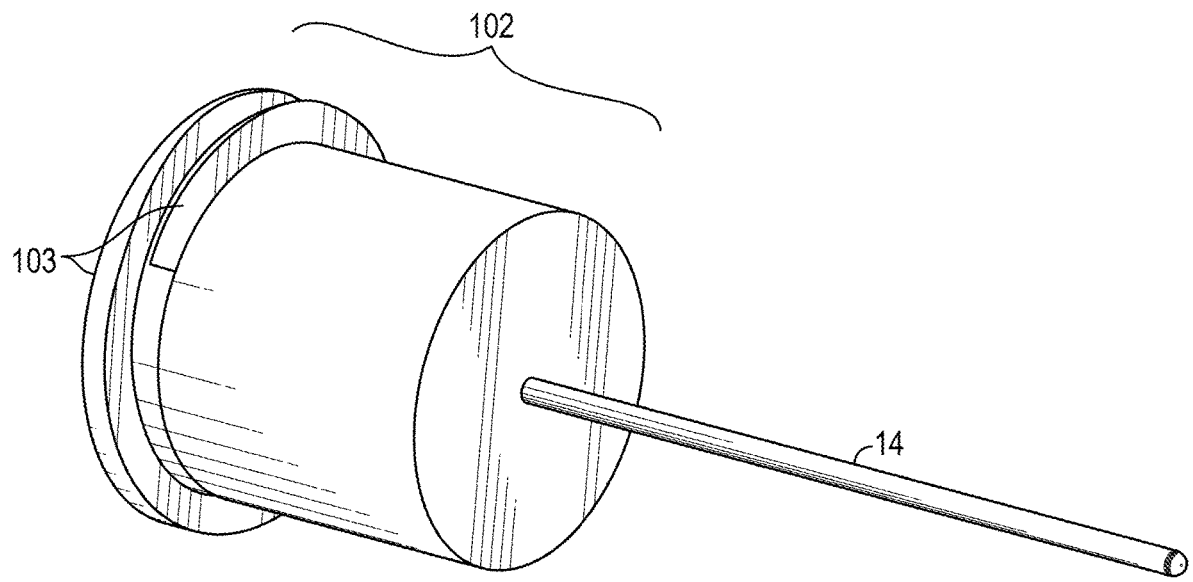
FIG. 2D is an enlarged view of a fastening mechanism of the microcannula of FIG. 2B, according to an illustrative implementation.

In some implementations, microcannula 14 may include one or more protrusions about the circumference of microcannula 14 (referred to herein as "circumferential protrusions"). Each circumferential protrusion may be spaced apart from another circumferential protrusion on microcannula 14 by a certain distance, such as a distance between about 40 μm and about 60 μm. In some implementations, each circumferential protrusion may be about 50 μm. Each circumferential protrusion may be of a certain height between about 15 μm and 35 μm. In some implementations, circumferential protrusions have height of 25 μm. Circumferential protrusions may be formed near the distal end of microcannula 14. In some implementations, circumferential protrusions may be formed starting from a location on microcannula 14 that is between about about 500 μm away and 250 µm away from the terminal end 98 of microcannula 14, for example, starting from about 350 µm away from the terminal end 98 of microcannula 14. Microcannula 14 may be formed of various materials including, but not limited to, polymethyl methacrylate (PMMA), polyimide, various types of silicones, such as high durometer silicone, and the like. Microcannula 14 may include or be coupled to a fastening mechanism. An example of such a fastening mechanism is a luer lock, such as luer lock 102, shown in FIG. 2D. In some implementations, the fastening mechanism may be configured with an external thread profile, such as the external thread profile 103 of luer lock 102 shown in FIG. 2D. In some implementations, microcannula 14 is attached or coupled to a fastening mechanism, such as a luer lock 102, at the proximal end of microcannula 14. In some implementations, connector body 26 may be configured to accept the fastening mechanism. For example, if the fastening mechanism includes an external thread profile, connector body 26 may be configured with an internal thread profile (not shown) near the distal end of connector body 26 to accept the fastening mechanism.

Figure 2E:
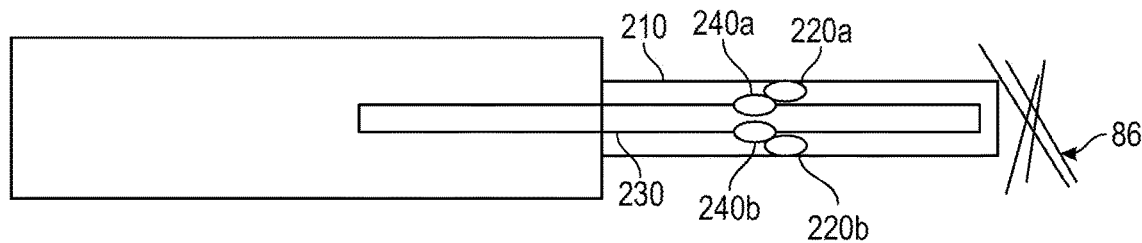
FIGS. 2E and 2F illustrate an exemplary device with multiple cannulas, according to an illustrative implementation.

In some implementations, exemplary device 10 may include multiple cannula and/or microcannula, such as outer cannula 210, inner cannula 230, as shown in FIG. 2E. Inner cannula 230 may be housed within outer cannula, as shown in FIG. 2E. In FIG. 2E, outer cannula 210 may have an outer diameter between 200 and 400 µm, such as about 250 µm, 300 µm, or 350 µm. In some implementations, outer cannula 210 has an inner diameter between 100 µm and 200 µm. Outer cannula 210 includes one or more protrusions, such as protrusions 220a, 220b, collectively protrusions 220. Protrusions 220 are located on the inside of the outer cannula 210, such as on the inner circumferential surface of the outer cannula 210. Protrusions 220 may be equidistantly or non-equidistantly spaced apart from each other. Protrusions 220 may be protruding notches, extensions, and the like. In some implementations, protrusions 220 extend towards each other. Outer cannula 210 is coupled to a distal end of handle 12, such as distal end 20 via connector 16. As described above, inner cannula 230 is housed within outer cannula 210. Inner cannula 230 is also housed within handle 12 and is configured to extend out from handle 12 and retract into handle 12. A control unit, such as actuator 38, is configured to control the extension and retraction of inner cannula 230.

Figure 2F:
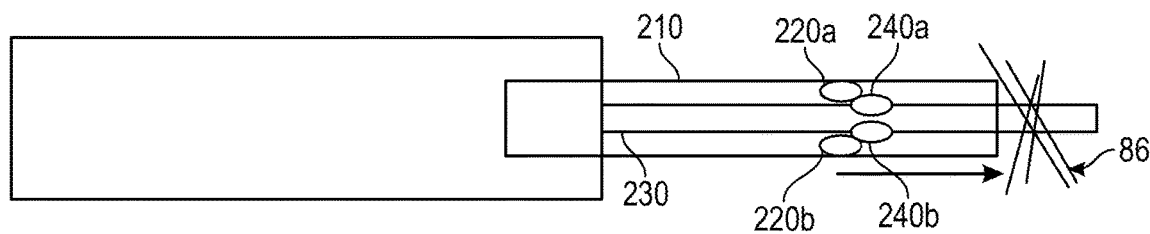
Figure 3A:
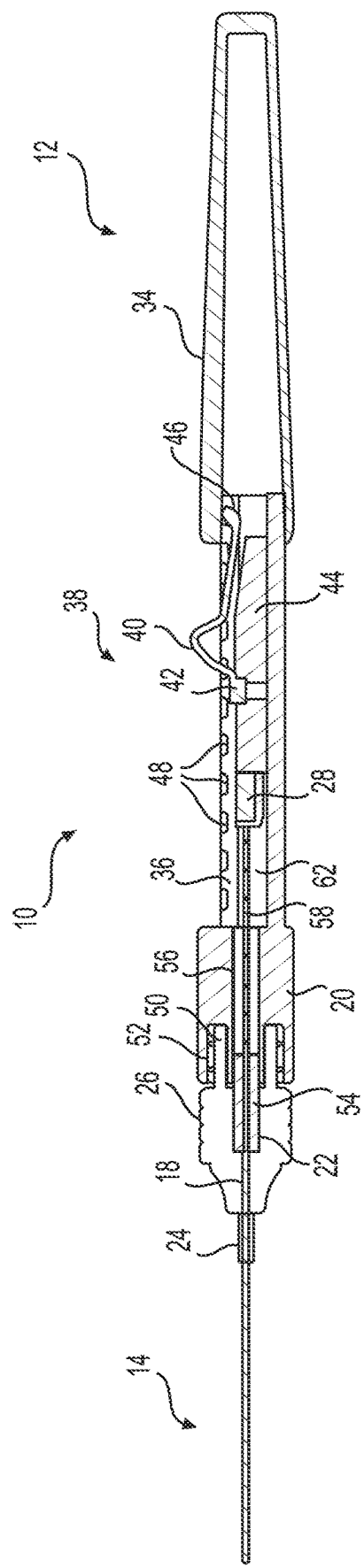
FIG. 3A illustrates a cross-sectional view of the exemplary device of FIG. 1, according to an illustrative implementation.

Inner cannula 230 includes one or more protrusions, such as protrusions 240a, 240b, collectively referred to herein as protrusions 240, as shown in FIG. 2E. Protrusions 240 may be equidistantly or non-equidistantly spaced apart from each other and located on the outer circumferential surface of inner cannula 230. Protrusions 240 may be located on the inner cannula 230 at locations that align with protrusions 220 such that protrusions 220 engage protrusions 240 when inner cannula 230 is extended out a certain distance from distal end of handle 12, such as distal end 20, and prevent inner cannula 230 from extending any further until a threshold amount of force is applied to an actuator to further extend the inner cannula 230. Application of threshold amount of force to the actuator extends the inner cannula 230 by causing protrusions 240 to depress protrusions 220. Protrusions 220 may be configured to be depressed into the outer cannula 210. Application of the threshold amount of force causes the inner cannula 230 to quickly penetrate trabecular meshwork 86, as shown in FIG. 2F. In some implementations, inner cannula 230 may include circumferential grooves, such as circumferential grooves 99a, 99b, and 99c, as shown in FIG. 2B. In some implementations, inner cannula 230 may include one or more orifices, such as orifices 32, positioned about the circumference of a distal end of inner cannula 230. The orifices of inner cannula 230 may be equidistantly or non-equidistantly spaced. In some implementations, orifices of inner cannula 230 are positioned about 180 degrees apart from each other about the circumference of distal end of inner cannula 230, similar to position of orifices 32, described above, and as shown in FIG. 2B. In some implementations, orifices of inner cannula 230 may be positioned at varying axial locations along distal end of inner cannula 230 and orifices of inner cannula 230 are arranged for delivery of a fluid (e.g., liquid or gas) or other substance from a reservoir, such as reservoir 28, as shown in FIG. 3A. In some implementations, the orifices of inner cannula 230 extend at an angle non-perpendicular or transverse to a central axis of inner cannula 230.

Handle 12 may have an ergonomic shape designed to be held comfortably in the hand, e.g., the palm of the dominate hand of a medical professional. Handle 12 may have a length between about 5 inches (12.7 cm) and about 10 inches (25.4 cm) Handle 12 may include a proximal end 34, distal end 20, and a channel or track 36 extending there between, as will be descried in further detail below. Proximal end 34 and distal end 20 have a generally circular cross-sectional shape. Alternatively, proximal end 34 and distal end 20 may have any other cross-sectional shape (e.g., oval, polygonal, irregular, etc.) without departing from the scope of this disclosure. In some arrangements, the cross-sectional shape of proximal end 34 and/or distal end 20 may vary along the length of handle 12 and/or be different from each other. Optionally, proximal end 34 may be tapered or narrowed in a proximal direction, as shown.

Figure 2G:
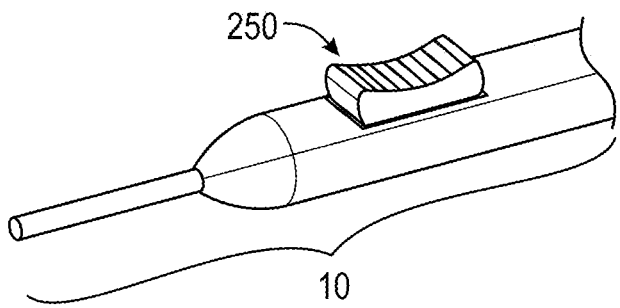
FIGS. 2G-2J illustrate various actuators included in exemplary device, according to an illustrative implementation.
Figure 2H:
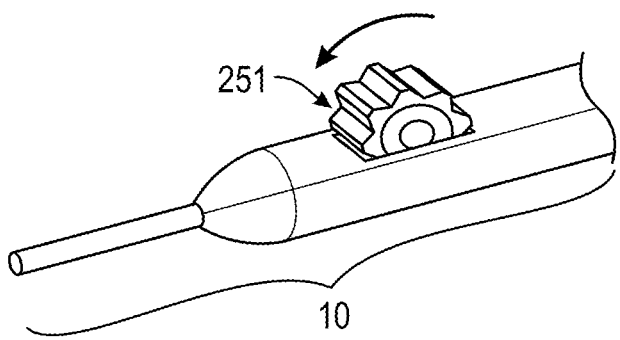
Figure 2I:
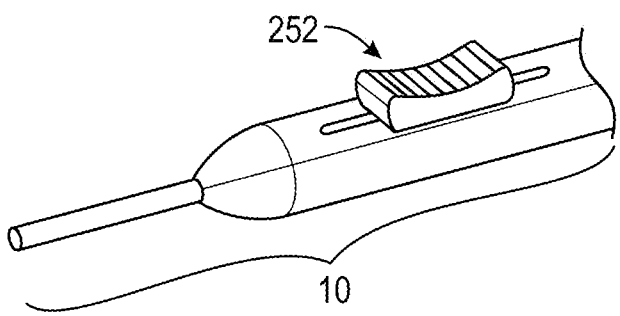
Figure 2J:
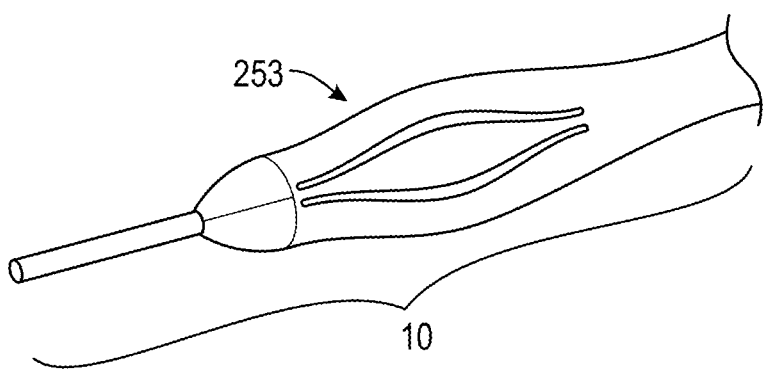

Handle 12 includes an actuator 38. Actuator 38 includes a button or slide 40 received within track 36 of handle 12. In some arrangements, slide 40 may be at least partially bent or folded, as shown in FIGS. 1 and 3. Alternatively, slide 40 may have any appropriate shape. A first end 42 (e.g., a distal end) of slide 40 may be fixedly (e.g., permanently fixed, non-separable, fixed throughout use, welded, glued, and/or heat staked, etc.) to a sled, carriage, and/or actuator body 44 movably positioned (e.g., slidably, translatable, etc.) within handle 12. For example, actuator body 44 may move, slide, or translate along an axis (e.g., a central longitudinal axis of handle 12 or an axis parallel thereto) with respect to handle 12, as will be described in further detail below. Additionally, a second end 46 (e.g., proximal end) of slide 40 includes a protrusion or projection sized to be received within track 36, as will be described in further detail below. As shown, second end 46 is angled, tapered, or slanted to facilitate movement along track 36, as will be described in further detail below. In some implementations, actuator 38 may be a push button, such as push button 250, as shown in FIG. 2G, a scroll wheel 251, as shown in FIG. 2H, a slider 252, as shown in FIG. 2I and the like. In some implementations, actuator 38 may be configured to be squeezed, such as actuator 253, as shown in FIG. 2J, to control delivery of fluid via microcannula 14.

Figure 2K:
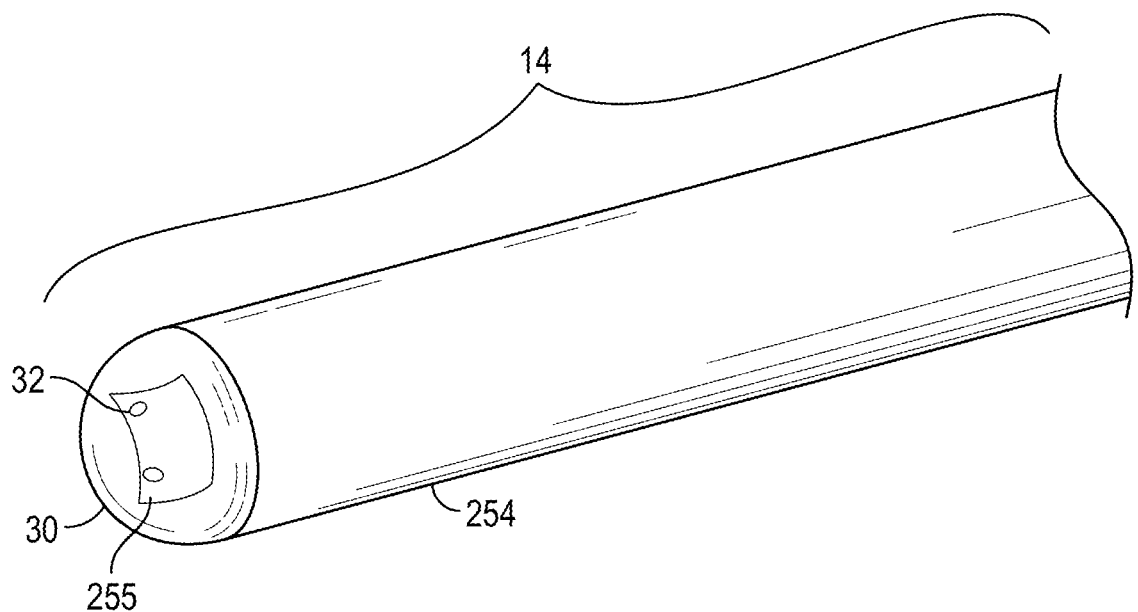
FIGS. 2K and 2L illustrate an exemplary device with an outer tube, according to an illustrative implementation.
Figure 2L:
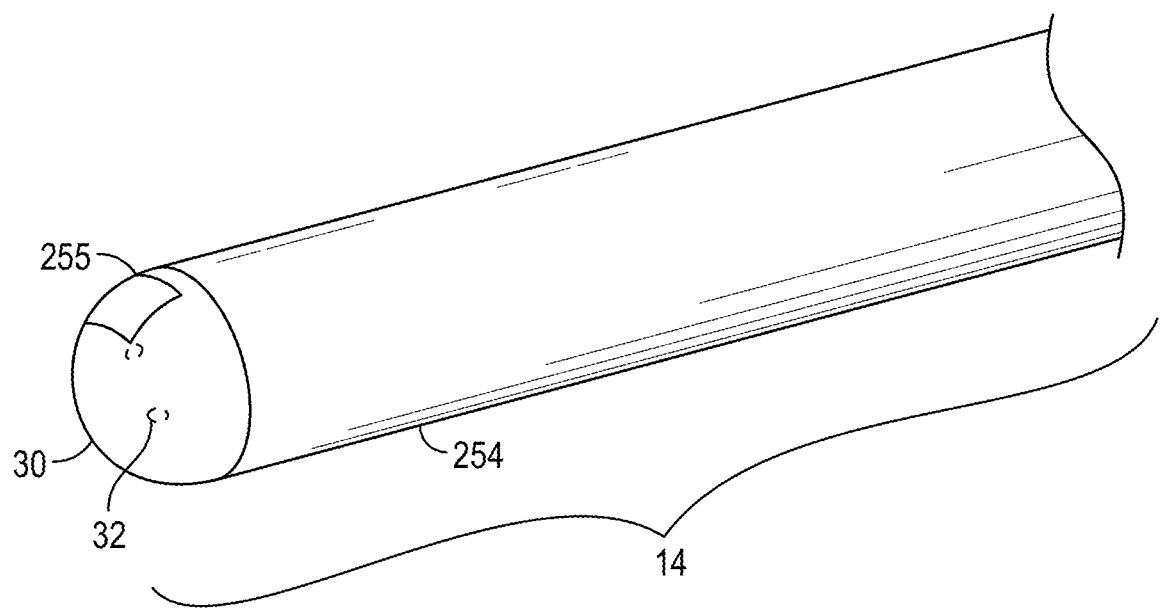

In some implementations, microcannula 14 is housed within an outer tube, such as outer tube 254, as shown in FIG. 2K. The outer tube 254 includes an opening or cut out such as opening 255. In some implementations, the opening or cutout 255 is located at the distal end of outer tube 254, as shown in FIG. 2K. The outer tube 254 extends to the handle 12 and is configured to be rotated by a control mechanism located proximal to the handle 12. Rotating the outer tube 254 may expose or hide one or more orifices on the microcannula 14, such as orifices 32 at the distal end. For example, as shown in FIG. 2L, rotating the outer tube 254, such that the opening 255 is moved from the position in FIG. 2K to the position in FIG. 2L, the orifices 32 exposed in FIG. 2K are now hidden in FIG. 2L.

Figure 2M:
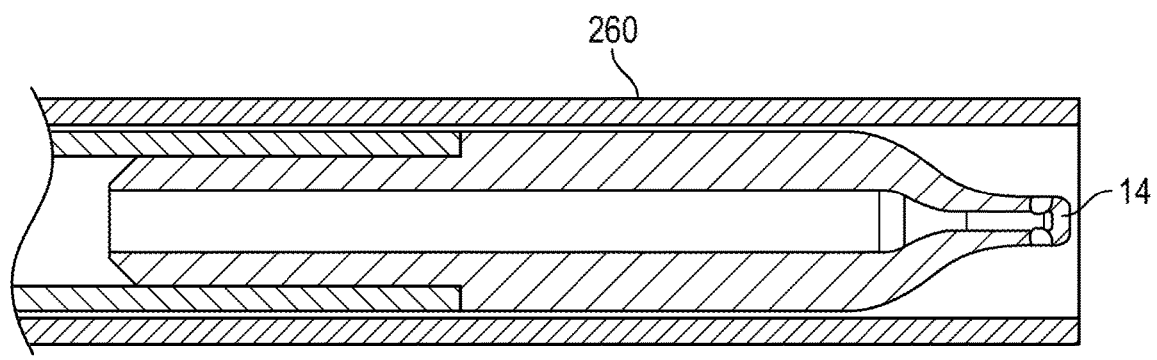
FIGS. 2M and 2N illustrate enlarged cross-sectional views of a microcannula and an outer sheath of the device of FIG. 1.
Figure 2N:
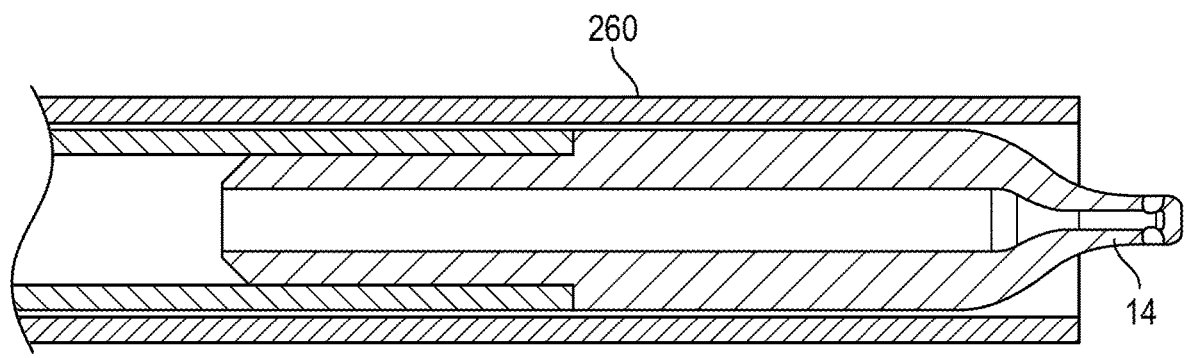

In some implementations, microcannula 14 is movably housed within an outer sheath, such as outer sheath 260, as shown in FIG. 2M. Microcannula 14 is configured to extend out of a distal end of outer sheath 260 in response to a user interaction with a control mechanism configured to extend and retract at least a portion of microcannula 14, such as the tip of microcannula 14, out of and in to outer sheath 260, respectively. For example, a user may apply a threshold amount of force to an actuator coupled to the microcannula 14, in the direction configured to cause the microcannula 14 to extend outside of the outer sheath 260, in order to extend the microcannula 14 outside of the outer sheath 260, as shown in FIG. 2N. In some implementations, the outer sheath 260 is configured to move in the direction proximal to a user of medical device 10 causing at least a portion of the microcannula 14, such as the tip of the microcannula 14, to be exposed outside of the outer sheath 260, as shown in FIG. 2N. The outer sheath 260 may move in the direction proximal to the user in response to pressing the distal portion of the outer sheath 260 against the trabecular meshwork of a patient.

The application of the threshold amount of force to an actuator coupled to the microcannula 14, causing at least a portion of the microcannula 14 to extend outside of the outer sheath 260, causes at least that portion of the microcannula 14 to penetrate the trabecular meshwork of a patient, such as trabecular meshwork 86 (shown in FIGS. 5A and 5B), when the microcannula 14 is advanced near the trabecular meshwork of the patient. Similarly, in implementations where the outer sheath 260 is configured to move in the direction proximal to a user of the medical device 10 in response to pressing the distal portion of the outer sheath 260 against the trabecular meshwork, the exposed portion of the microcannula 14 or a portion of the exposed portion of the microcannula 14 may penetrate the trabecular meshwork.

Track 36 extends through a radially outer wall of handle 12 with respect to the central longitudinal axis of handle 12. Accordingly, slide 40 may extend radially outwardly of the center axis through track 36. As shown, track 36 may be notched such that pairs of inwardly protruding notches, extensions, or flanges 48 extend towards each other to narrow a width of track 36 at a plurality of axially spaced locations along the length of track 36. In other words, track 36 extends longitudinally along handle 12 and has a width, extending in a direction perpendicular the longitudinal length of track 36. The width of track 36 varies along the length of the track 36 such that each location of track 36 having a pair of flanges 48 has a smaller or more narrow width than a width of track 36 at a location devoid of one or more flanges 48. An axial spacing between adjacent pairs of flanges 48 may directly correlate to an amount of a single dose or quantity of a substance (e.g., a fluid or gas) for injection via microcannula 14, as will be described in further detail below. Additionally, it is understood that slide 40 may be replaced with any appropriate actuator, e.g., wheel, button, toggle, or the like, without departing from the scope of this disclosure.

Figure 4A:
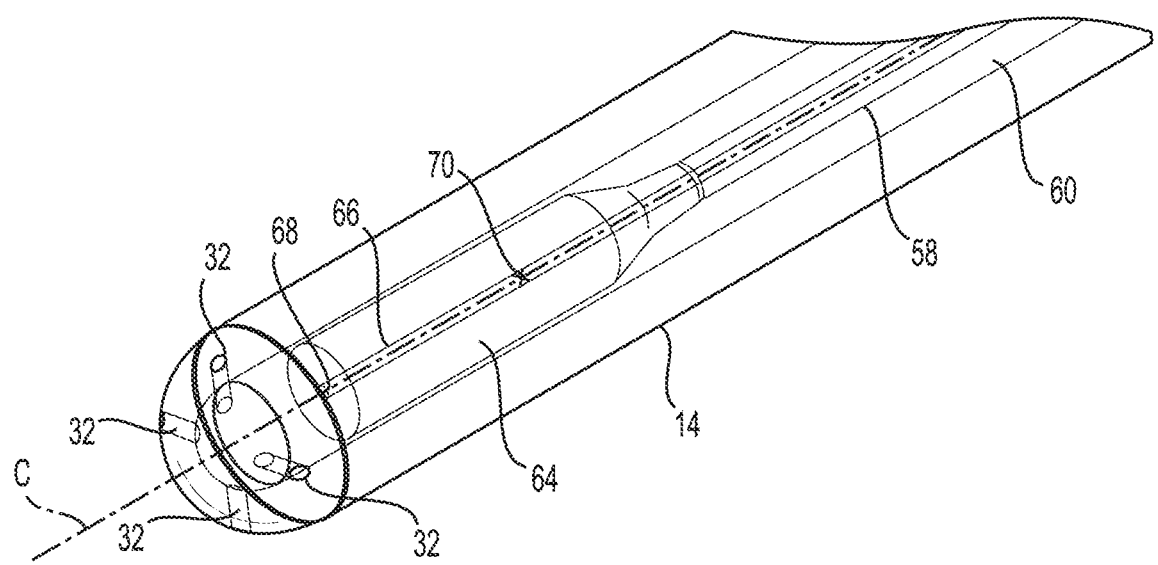
FIG. 4A illustrates a perspective view of the microcannula of the device of FIG. 1, according to an illustrative implementation.

Turning to FIGS. 3A and 4A, as noted above, connector 16 facilitates coupling between microcannula 14 and handle 12. For example, a proximal end 50 of connector 16 may be received radially within a cavity 52 of distal end 20 of handle 12. Proximal end 50 and cavity 52 may be correspondingly threaded to facilitate secure engagement therebetween. As noted above, proximal end 18 of microcannula 14 extends through lumen 22 of connector 16 and may be fixedly coupled (e.g., glued, welded, or otherwise secured) to connector 16. Additionally, connector 16 includes a tube, shaft, or other such support 54 received within lumen 22 of connector 16, and within a lumen 56 of distal end 20 of handle 12.

A piston assembly including a piston rod 58 extends proximally through a central lumen 60 of microcannula 14, through lumen 22 of connector 16, through lumen 56 of distal end 20 of handle 12, and towards actuator body 44 housed within a cavity 62 of handle 12. Piston rod 58 may be reciprocally disposed within central lumen 60. A proximal end of piston rod 58 is fixedly coupled to actuator body 44 such that distal advancement of actuator body 44 will result in likewise distal advancement of piston rod 58. As shown in FIG. 4A, piston rod 58 is coupled to a piston head 64 and is axially moveable relative to central lumen 60 of microcannula 14. A piston passage 66 extends through piston rod 58, through piston head 64, and terminates distally in a piston orifice 68. A one-way or other suitable valve 70 may be arranged within the piston passage 66 to prevent, inhibit, or block backflow of fluid or other substances, e.g., proximally directed flow.

In order to deliver fluid or other substances from reservoir 28, a medical professional may advance slide 40 distally towards microcannula 14. Due to the connection between first end 42 and actuator body 44, and the connection between actuator body 44 and piston rod 58, distal advancement of slide 40 advances piston head 64 towards orifices 32 to deliver fluid or other substances within central lumen 60 through orifices 32. Any appropriate mechanism may be used to urge fluid or substances within reservoir 28 through the piston passage 66, through the one-way valve 70 within the piston passage 66, and into the cavity 60. For example, reservoir 28 may be compressed thereby pushing fluid or other substances into and through the piston passage 66. Alternatively, fluid or other substances may be drawn through piston passage 66 via capillary action, via a micro pump (e.g., a MEMS pump) or any other suitable pump (not shown).

Figure 3B:
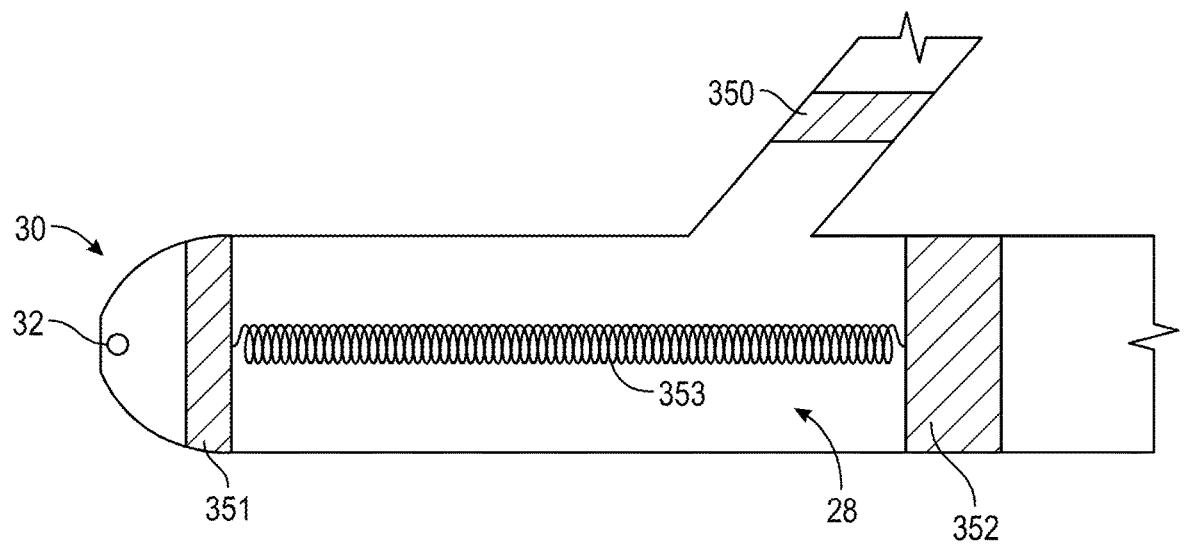
FIG. 3B illustrates a cross-sectional view of a reservoir of the exemplary device of FIG. 1, according to an illustrative implementation.

In some implementations, as shown in FIG. 3B, a fill port 350 may be in fluid communication with reservoir 28 and visco may be injected into the reservoir 28 via the fill port. A one-way valve 351 may be attached to a distal end of the reservoir 28 and a plunger 352 may be attached to a proximal end of reservoir 28. A valve spring 353 is coupled to plunger 352 and one-way valve and 351. Actuation or compression of plunger 352 compresses visco and opens the one-way valve 351, causing visco to eject through an orifice 32 on the distal end 30 of microcannula 14. Plunger 352 may be actuated mechanically or electrically. In some implementations, plunger 352 may be actuated by a gas, such as carbon dioxide, CO2. In some implementations plunger 352 may be coupled to a phaco system and actuated by the phaco system.

Figure 3C:
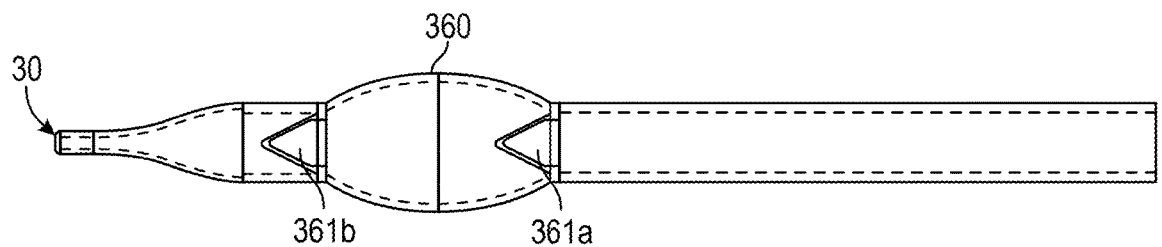
FIG. 3C illustrates a cross-sectional view of another implementation of the exemplary device of FIG. 1, according to an illustrative implementation.

In some implementations, handle 12 may include a visco bag and a button communicatively coupled to the visco bag with the visco bag in communication with an orifice 32 on the distal end 30. Depression of the button compresses visco bag and causes visco fluid to eject through the orifice 32 on the distal end 30. In some implementations, as shown in FIG. 3C handle 12 includes a flexible bulb 360 in communication with one-way valves 361a, 361b. Compression of the flexible bulb causes the one-way valves to open and visco in the handle 12 to be directed to an orifice 32 at the distal end 30.

As shown in FIG. 4A, each orifice 32 may be a channel angled relative to an axis of the microcannula 14, such as the central axis C of the microcannula 14. As described above, an orifice 32 may extend at an angle perpendicular or non-perpendicular to an axis of the microcannula 14, such that the channel is angled perpendicularly or non-perpendicularly to the axis of the microcannula 14. In addition, each orifice may have one or more openings having a tapered configuration. For example, a first end (e.g., a radially inner end) of each orifice 32 may be positioned at a first axial location along the length L of microcannula 14 while a second end (e.g., a radially outer end) of each orifice 32 may be positioned at a second axial location along the length L of microcannula 14. In some embodiments, the second axial location may be proximal of the first axial location. In other embodiments, the second axial location may be distal to the first axial location. In such a manner, a channel defined by each orifice 32 may be angled relative to central longitudinal axis C. In other words, the first end of each orifice 32 is positioned radially closer to the central longitudinal axis C (and distally or proximally of the second end of each orifice 32 along an axis parallel to central longitudinal axis C), while the second end of each orifice 32 is positioned radially farther away from central longitudinal axis C (and proximally or distally of the first end of each orifice 32 along an axis parallel to central longitudinal axis C). For example, a channel defined by orifice 32 may extend at an angle α relative to central longitudinal axis C of between about 5° and about 45° degrees. Accordingly, during delivery of fluid or other substance from central lumen 60 through orifices 32, the fluid or other substance will necessarily flow proximally (e.g., from a distal location towards a proximal location) or distally and radially away from microcannula 14.

As noted above, axial spacing between adjacent pairs of flanges 48 of track 36 correlates to an amount of a single dose or quantity of fluid or other substance for injection via microcannula 14. For example, before advancement of slide 40, second end 46 of slide 40 is positioned between two adjacent first pairs of flanges 48, thus preventing inadvertent advancement (or retraction) of slide 40 and injection of fluid or other substances through orifices 32. To advance slide 40 and inject fluid or other substances via orifices 32, a medical professional must first overcome the resistance provided by the two adjacent first pairs of flanges 48 against the second end 46 of slide 40, and then continue advancing slide 40 to push or urge fluid or other substances in central lumen 60 distal of piston head 64 through orifices 32. That is, as slide 40 is urged distally forward, the angled or slanted surface of second end 46 will slide or move along surfaces of flanges 48 until second end 46 deflects radially inwardly towards the central axis of handle 12 and is positioned underneath flanges 48, at which point slide 40 can continue advancement distally.

As slide 40 continues distal advancement, second end 46 may be received between two adjacent second pairs of flanges 48 and retained therein, thus preventing further inadvertent advancement. For example, second end 46 may deflect radially outwardly away from the central axis of handle 12 (returning towards an undeflected orientation). It is understood, second end 46 may be biased radially outwardly toward the undeflected orientation. The two second adjacent pairs of flanges 48 may be adjacent (e.g., next to) the two adjacent first pairs of flanges 48. In other words, as slide 40 is advanced distally, interaction between second end 46 and each two adjacent pairs of flanges 48 will cause an increase of resistance exerted to the medical professional, thereby resulting in a tactile indication that a specified dose or amount of fluid or substance has been delivered through orifices 32.

In some implementations, as shown in the exploded view of FIG. 4B, the tip of microcannula 14 includes a machined cap 401 that may be laser welded on to the tip of microcannula 14, as shown in FIG. 4C. In some implementations, as shown in the exploded view of FIG. 4D, wire 402 may be adhered to the tip of the microcannula 14 using an adhesive material, such as epoxy. The resulting tip shown in FIG. 4E. In some implementations, wire may be laser welded on to the tip of microcannula 14. Tip of microcannula 14 may be encapsulated with silicone over mold 403, in some implementations, as shown in FIG. 4F and in the rotated view of FIG. 4G. The silicon overmold 403 may include one more slits 404 in some implementations, as shown in FIG. 4H. In some implementations, as shown in the exploded view of FIG. 4I, polyimide overmold 406a and 406b, and a core pin 405 may be used to encapsulate the tip of the microcannula 14, resulting in the microcannula 14 and tip configuration, as shown in the 90 degrees rotated view of FIG. 4J. In some implementations, tip of microcannula 14 is configured with soft polymer material to prevent penetration into certain portions of the patient, such as sclera. In some implementations, tip of microcannula 14 includes a light source, such as a light emitting diode, which is configured to produce light at the trabecular meshwork in response to receiving an input to produce light, such as powering on the light source.

In some implementations, microcannula 14 includes a nitinol (NiTi) tube at the distal end of microcannula 14. The NiTi tube may be configured to the The NiTi tube at the distal end is configured to one bend in a certain direction after the NiTi tube travels a certain distance. In some implementations, handle 12 includes a control mechanism coupled to the NiTi tube and the control mechanism is configured to rotate NiTi tube 180 degrees in response to receiving an input or a user interacting with the control mechanism.

Figure 5A:
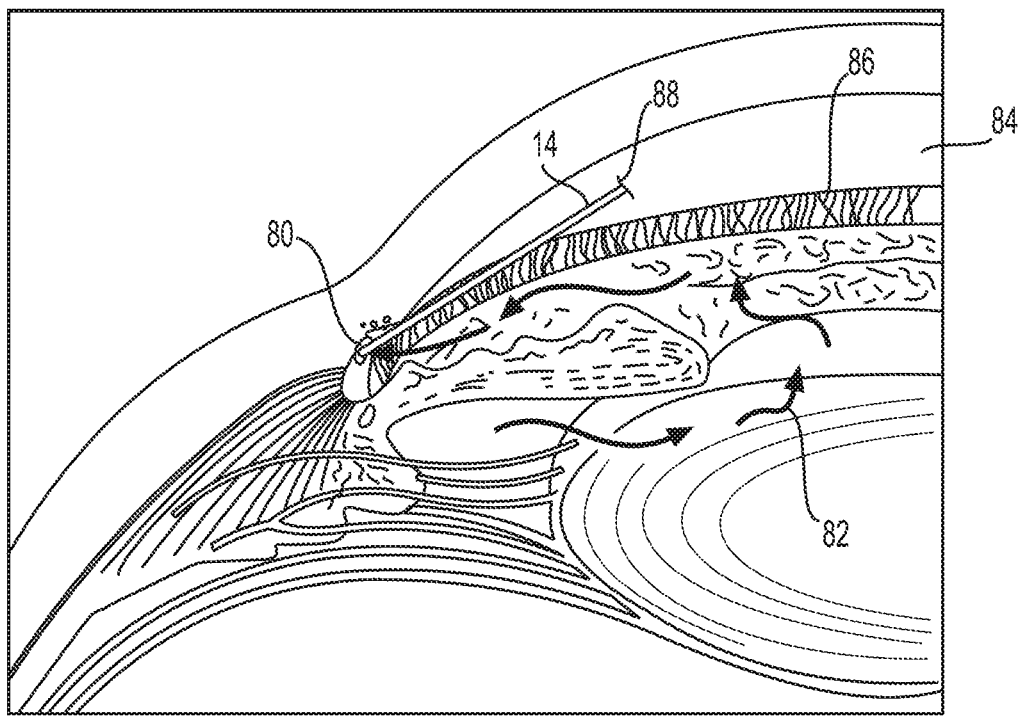
FIGS. 5A and 5B illustrate an exemplary method of using the device of FIG. 1, according to an illustrative implementation.
Figure 5B:
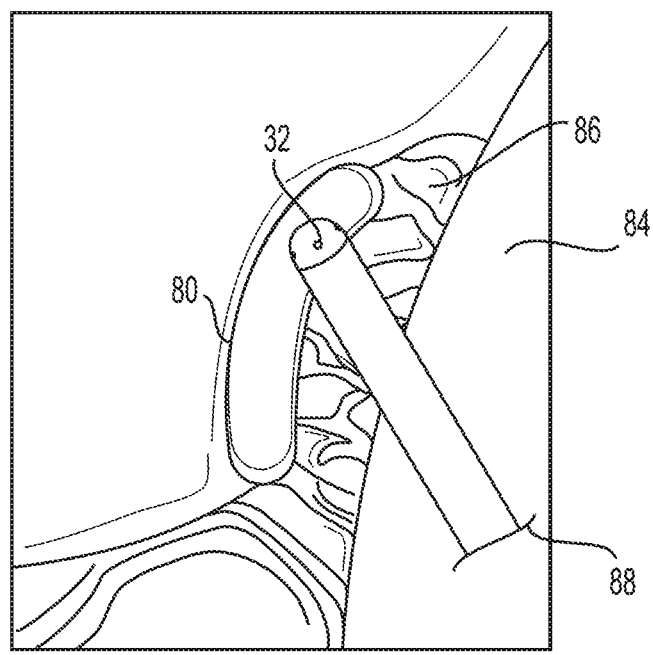

FIGS. 5A and 5B illustrate an exemplary method of using device 10 to deliver a substance (e.g., a fluid or gas) into, e.g., Schlemm's canal 80 or any other suitable portion of a patient's eye. As noted above, in a healthy eye, a stream of aqueous humor 82 drains out of the anterior chamber 84 of the eye, through the trabecular meshwork 86 and then into Schlemm's canal 80 and distal collector channels. The aqueous humor 82 then exits through Schlemm's canal 80 into the collector channels and distal venous system. When this flow path of aqueous humor 82 is interrupted (e.g., due to diseased or damaged tissue in the trabecular meshwork 86 and/or Schlemm's canal 80), the IOP of an eye may rise, potentially resulting in a variety of medical concerns (e.g., glaucoma, loss of vision, optic nerve damage, etc.). In order to improve the flow path of aqueous humor 82, a medical professional may insert microcannula 14 through an incision 88 made in the anterior chamber 84 and advance distal end 30 of microcannula 14 through the trabecular meshwork 86 and into Schlemm's canal 80, as shown in FIG. 5A. Optionally, distal end 30 may be curved such that insertion of microcannula 14 into Schlemm's canal 80 may be accomplished by inserting distal end 30 tangentially to Schlemm's canal 80 (e.g., in a manner similar to that of insertion of an IV needle into a vein) rather than directly pushing into Schlemm's canal 80 via the distal-most end of microcannula 14.

Turning now to FIG. 5B, once distal end 30 of microcannula 14 is inserted into Schlemm's canal 80 such that each orifice 32 is fully housed within Schlemm's canal 80, the medical professional may inject a pre-defined dose or amount of fluid or other substance from reservoir 28 via actuation of slide 40 (FIGS. 1, 3A, and 4A) as discussed above. Further, since advancement of slide 40 is limited due to the interaction of second end 46 and flanges 48, each pre-defined dose or amount of fluid or substance to be injected upon each incremental advancement of slide 40 is accurate and precise. For example, each "dose" may be 200 microliters+/−50 microliters.

After injection of a pre-defined dose or amount of fluid or other substance through orifices 32 (FIGS. 2A and 4A), microcannula 14 may be rotated between about 50° and about 120°, e.g., between about 60° and about 90° about central axis C (FIG. 4A) of microcannula 14. Once rotated, the medical professional may inject an additional pre-defined dose or amount of fluid or other substance from reservoir 28 via actuation of slide 40 (FIGS. 1, 3, and 4) as discussed above. This process may be repeated any appropriate number of times, e.g., about six times, and then microcannula 14 may be removed from incision 88.

Optionally, after the injection of one or more pre-defined doses of fluid or other substance at a certain location within Schlemm's canal 80 (e.g., without relocating (other than rotating) distal end 30 of microcannula 14), distal end 30 may be retracted and repositioned within the eye. In some arrangements, such repositioning may occur via withdrawal of microcannula 14 from incision 88 (e.g., a first incision 88), and reinsertion through an additional incision 88, spaced from the first incision 88. In some implementations, fluid may be delivered into the Schlemm's canal 80 and trabecular meshwork 86 simultaneously, causing the Schlemm's canal 80 to open and deliver the fluid into the various layers of the trabecular meshwork 86. Alternatively, such repositioning may include retraction of distal end 30 from Schlemm's canal 80 and/or trabecular meshwork 86 and then relocation into a new portion of Schlemm's canal 80 without removal of microcannula 14 from the first incision 88. In either case, distal end 30 of microcannula 14 may be positioned approximately 30-90° away from the original insertion site.

The substance located within reservoir 28, and injected via orifices 32 may be any appropriate substance. For example, the substance may comprise viscoelastic fluid such as, e.g., sodium hyaluronate and chondroitin sulfate. Viscoelastic fluid is a highly pliable, gel-like material which helps provide enough space for adequate drainage and eye pressure relief by expanding tissue structures away from one another, to re-open or expand a flow path of aqueous humor 82. Viscoelastic fluid also may clear an obstructed view by expanding bleeding structures away from one another to improve visualization.

In another arrangement, reservoir 28 may be filled with stem cells, medicaments, a gas (e.g., SF6 or C3F8), and/or dyes (e.g., trypan blue dye). Injected dye, for example, will flow through the trabecular meshwork 86, enhancing visualization of aqueous humor 82 fluid flow to determine which areas, if any, of the trabecular meshwork 86 remain blocked, collapsed, or otherwise impede flow of aqueous humor 82. Injected stem cells, on the other hand, may initiate growth of healthy tissues within the eye (e.g., to develop healthy trabecular meshwork 86 to enhance drainage of aqueous humor 82 there through).

In some arrangements, a first substance is injected into one or more locations of the eye, the reservoir 28 is refilled with a second substance different than the first substance, and then the second substance is injected into one or more locations of the eye. Additionally, this process may be repeated as necessary to deliver each selected substance. For example, as noted above one or both of connector 16 and distal end 20 may include a fluid luer port (not shown), through which reservoir 28 may be selectively refilled. Accordingly, a plurality of substances, e.g., viscoelastic, medicament, stem cells, and dye, may be injected into the eye of a patient to achieve a desired result (e.g., visualize the flow path of aqueous humor 82, expand Schlemm's canal 80, promote tissue regrowth, or to otherwise medicinally treat diseased tissue). Accordingly, during a procedure, a single (e.g., only one) incision 88 may be needed to deliver a variety of substances as deemed necessary and/or beneficial by the medical professional, thus reducing trauma, recovery time, medical professional time, and associated fees, etc.

It is to be understood that while the foregoing description describes devices and methods for injection of a fluid or other substance through orifices 32, the disclosure is not so limited. Indeed, device 10 described herein may be arranged for precision-controlled aspiration of fluid or other substances away from the eye. For example, rather than distal advancement of slide 40 to incrementally inject a pre-defined "dose" or quantity of a substance or fluid radially outwardly of microcannula 14 via orifices 32, proximal retraction of slide 40 may incrementally draw (e.g., suction, pull, etc.) fluid or other substances (e.g., tissue, blood, aqueous humor 82, etc.) out of Schlemm's canal 80 for removal from the eye. In other words, device 10 may be actuated in a reverse manner from that described above to achieve a removal of fluid or other substances from the eye. In arrangements in which device 10 is positioned for removal of fluid or other substances from the eye, one or more components of device 10 may be reversed (e.g., one-way valve 70 may be oriented to permit proximal flow of fluid or other substance while preventing distal flow of fluid or other substance along piston passage 66, etc.). In some embodiments, microcannula 14 may be operably coupled to a suitable vacuum source for the generation of suction.

Device 10 may be comprised of any appropriate materials. For example, microcannula 14 may include one or more of metals (e.g., stainless steel, titanium, nitinol, etc.) or a rigid (e.g., sufficiently rigid to push through trabecular meshwork 86 and Schlemm's canal 80 without bending or otherwise deforming) polymer (e.g., PEEK, Polyimide, etc.). Exemplary materials also may include polymers transparent to optical coherence tomography (OCT) (e.g., glycol modified polyethylene terephthalate, polyvinal chloride, polymethyl methacrylate, and/or polyphenylsulfone, etc.) such that imaging via OCT can be done simultaneously with positioning of microcannula 14 and/or injection of a substance via orifices 32 while minimally disrupting the images obtained via OCT.

Additionally, any one or more portions of microcannula 14, e.g., distal end 30, may be radiopaque to enhance visualization by a medical professional during a procedure. Likewise, handle 12 may include any one or more metals or polymers, as appropriate. Additionally or alternatively, distal end 30 may include a light-emitting diode (LED) (not shown). When the LED is lit, the medical professional may be able to see the light through the sclera of the eye, giving the user an indication of the position of microcannula 14 in the eye. In some arrangements, one or more radiopaque indicia or other markings may be located at distal end 30 of microcannula 14 to facilitate visualization of the depth of microcannula 14 into the eye of the patient. Additionally, microcannula 14 may include a cutting device (e.g., knife, blade, point tip, etc.) (not shown) adjacent distal end 30. In use, such a cutting device may enable a medical professional to cut tissue (e.g., trabecular meshwork 86 and/or Schlemm's canal 80) prior to or following injection of a substance via orifices 32. For example, microcannula 14 including the cutting device may be moved side-to-side to cut the tissue lifted due to injection of the substance via orifices 32.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A medical device comprising: a microcannula having a proximal end, a distal tip, and a cavity, the microcannula having a central longitudinal axis; a handle coupled to the proximal end of the microcannula; multiple orifices extending circumferentially about the distal tip of the microcannula, each of the multiple orifices defining a channel extending transverse to the central longitudinal axis and having a radially outer end positioned radially farther away from the central longitudinal axis than a radially inner end, and each of the multiple orifices configured to deliver a substance radially outwardly from the distal tip of the microcannula; and a plurality of grooves about a circumference of the microcannula, wherein an inner diameter of the microcannula tapers down from a first position of the microcannula to a second position of the microcannula closer to the distal tip than the first position, the inner diameter and an outer diameter of the microcannula varying at a same rate along a length of the microcannula.

2. The medical device of claim 1, wherein a first orifice of the multiple orifices is spaced 180 degrees apart from a second orifice of among, the multiple orifices.

3. The medical device of claim 1, wherein each of the plurality of grooves has a depth between 15 μm and 35 μm.

4. The medical device of claim 1, wherein each of the plurality of grooves is formed proximal to the multiple orifices.

5. The medical device of claim 1, wherein the substance is a viscoelastic fluid, wherein the handle comprises a reservoir containing the viscoelastic fluid, and an actuator configured to eject the viscoelastic fluid radially outwardly through the multiple orifices.

6. The medical device of claim 1, wherein the radially outer end is positioned distal to the radially inner end, such that each of the multiple orifices are configured to deliver the substance distally and radially outwardly from the microcannula.

7. A medical device comprising: a first cannula having a distal end, and a cavity, the first cannula having a central longitudinal axis, and one or more protrusions, the one or more protrusions of the first cannula extending circumferentially at the distal end of the first cannula and located in the cavity of the first cannula; a second cannula having a proximal end, a distal tip, and a cavity, the second cannula being a microcannula moveably housed within the first cannula and having a central longitudinal axis, and one or more protrusions located on an outer circumferential surface of the second cannula; multiple orifices extending circumferentially about the distal tip of the microcannula, each of the multiple orifices defining a channel extending transverse to the central longitudinal axis of the microcannula and having, a radially outer end positioned radially farther away from the central longitudinal axis of the microcannula than a radially inner end, and each of the multiple orifices configured to deliver a substance radially outwardly from the distal tip of the microcannula; and a plurality of grooves about a circumference of the second cannula, wherein an inner diameter of the second cannula tapers down from a first position of the second cannula to a second position of the second cannula closer to the distal tip than the first position, the inner diameter and an outer diameter of the second cannula varying at a same rate along a length of the second cannula.

8. The medical device of claim 7, wherein a first orifice of the multiple orifices is positioned parallel to a second orifice of the multiple orifices.

9. The medical device of claim 7, wherein the plurality of grooves are located at the distal tip of the second cannula.

10. The medical device of claim 7, wherein the plurality of grooves are equidistantly spaced apart.

11. The medical device of claim 7, wherein the one or more protrusions of one of the first cannula and the second cannula include multiple protrusions equidistantly spaced apart.

12. The medical device of claim 7, wherein the one or more protrusions of the second cannula are proximal to the one or more protrusions of the first cannula when the distal tip of the second cannula is within the first cannula.

13. The medical device of claim 7, wherein the one or more protrusions of the second cannula are distal to the one or more protrusions of the first cannula when at least a portion of the distal tip of the second cannula is moved outside of the distal end of the first cannula.

14. A method of delivering fluid, comprising:
inserting a microcannula through an incision in an anterior chamber of an eye, the microcannula including a proximal end, a distal tip, and a cavity, the microcannula having a central longitudinal axis with the proximal end of the microcannula being coupled to a handle, wherein an inner diameter of the microcannula tapers down from a first position of the microcannula to a second position of the microcannula closer to the distal tip than the first position, the inner diameter and an outer diameter of the microcannula varying at a same rate along a length of the microcannula; advancing the distal tip of the microcannula through a trabecular meshwork of the eye and into Schlemm's canal of the eye;
and delivering fluid through multiple orifices each of which being positioned within the Schlemm's canal, the multiple orifices extending circumferentially about the distal tip of the microcannula, each of the multiple orifices defining a channel extending transverse to the central longitudinal axis and having a radially outer end positioned radially farther away from the central longitudinal axis than a radially inner end such that the fluid is delivered radially outwardly from the distal tip of the microcannula.

15. The method of claim 14, wherein a plurality of grooves are located at the distal tip of the microcannula.

16. The method of claim 14, wherein the microcannula includes one or more protrusions located on an outer circumferential surface of the microcannula; and
wherein the microcannula is movably housed within a second cannula, the second cannula having one or more protrusions extending circumferentially at a distal end of the second cannula and located in a cavity of the second cannula.

17. The method of claim 16, wherein advancing the distal tip of the microcannula further comprises:
applying a force to the microcannula to move the one or more protrusions of the microcannula distal to the one or more protrusions of the second cannula.

18. The method of claim 14, wherein delivering the fluid through the multiple orifices includes delivering the fluid into the Schlemm's canal and one or more layers of the trabecular meshwork.

* * * * *